(12) United States Patent
Friedling

(10) Patent No.: US 11,357,982 B2
(45) Date of Patent: Jun. 14, 2022

(54) WIRELESS STREAMING SOUND PROCESSING UNIT

(71) Applicant: Cochlear Limited, Macquarie University (AU)

(72) Inventor: Jan Patrick Friedling, Grose Vale (AU)

(73) Assignee: Cochlear Limited, Macquarie University (AU)

( * ) Notice: Subject to any disclaimer, the term of this patent is extended or adjusted under 35 U.S.C. 154(b) by 82 days.

(21) Appl. No.: 16/758,591

(22) PCT Filed: Oct. 23, 2018

(86) PCT No.: PCT/IB2018/058247
§ 371 (c)(1),
(2) Date: Apr. 23, 2020

(87) PCT Pub. No.: WO2019/082075
PCT Pub. Date: May 2, 2019

(65) Prior Publication Data
US 2021/0187293 A1  Jun. 24, 2021

Related U.S. Application Data

(60) Provisional application No. 62/576,761, filed on Oct. 25, 2017.

(51) Int. Cl.
*H04R 25/00* (2006.01)
*A61N 1/36* (2006.01)
*A61N 1/372* (2006.01)

(52) U.S. Cl.
CPC ..... *A61N 1/36036* (2017.08); *A61N 1/37252* (2013.01); *H04R 25/505* (2013.01); *H04R 25/552* (2013.01); *H04R 25/554* (2013.01)

(58) Field of Classification Search
CPC ............ A61N 1/36036; A61N 1/37252; H04R 25/554; H04R 25/552; H04R 25/505
See application file for complete search history.

(56) References Cited

U.S. PATENT DOCUMENTS 9,179,222 B2 * 11/2015 Hillbratt ................ H04R 25/43
9,544,699 B2 *  1/2017 Haubrich ............. H04B 7/0613
(Continued)

FOREIGN PATENT DOCUMENTS

| CN | 101843118 A | 9/2010 |
| CN | 102105192 A | 6/2011 |
| CN | 107071674 A | 8/2017 |

OTHER PUBLICATIONS

International Search Report and Written Opinion received in related international application No. PCT/IB2018/058247, dated Feb. 15, 2019, (14 pages).

*Primary Examiner* — Brian Ensey
(74) *Attorney, Agent, or Firm* — Edell, Shapiro & Finnan, LLC

(57) ABSTRACT

At least one of the first or second hearing prostheses of a binaural hearing prosthesis system includes a dual-mode sound processing unit that is configured to selectively operate in a "sound processing mode" or in a "wireless streaming mode." When operating in the sound processing mode, the dual-mode sound processing unit is configured to convert received sound signals into output signals for use in stimulating a first ear of a recipient. However, while operating in the wireless streaming mode, the dual-mode sound processing unit is configured to capture input signals (e.g., sound signals, data signals, etc.) and to encode those input signals for direct or indirect wireless transmission to the sound processing unit of the other hearing prosthesis of the binaural hearing system.

31 Claims, 11 Drawing Sheets

(56) References Cited

U.S. PATENT DOCUMENTS

| | | | |
|---|---|---|---|
| 10,142,740 B2* | 11/2018 | Ridler | A61N 1/36038 |
| 2007/0230714 A1 | 10/2007 | Armstrong | |
| 2009/0030484 A1 | 1/2009 | Chambers | |
| 2011/0103626 A1* | 5/2011 | Bisgaard | H04R 3/005 |
| | | | 381/313 |
| 2014/0155686 A1 | 6/2014 | Meskens | |
| 2014/0270212 A1 | 9/2014 | Ridler et al. | |
| 2014/0270296 A1 | 9/2014 | Fort et al. | |
| 2015/0326984 A1 | 11/2015 | Haubrich et al. | |
| 2016/0227332 A1 | 8/2016 | Pedersen et al. | |
| 2016/0286323 A1 | 9/2016 | Buehl | |
| 2017/0143962 A1* | 5/2017 | Mishra | A61N 1/0541 |

* cited by examiner

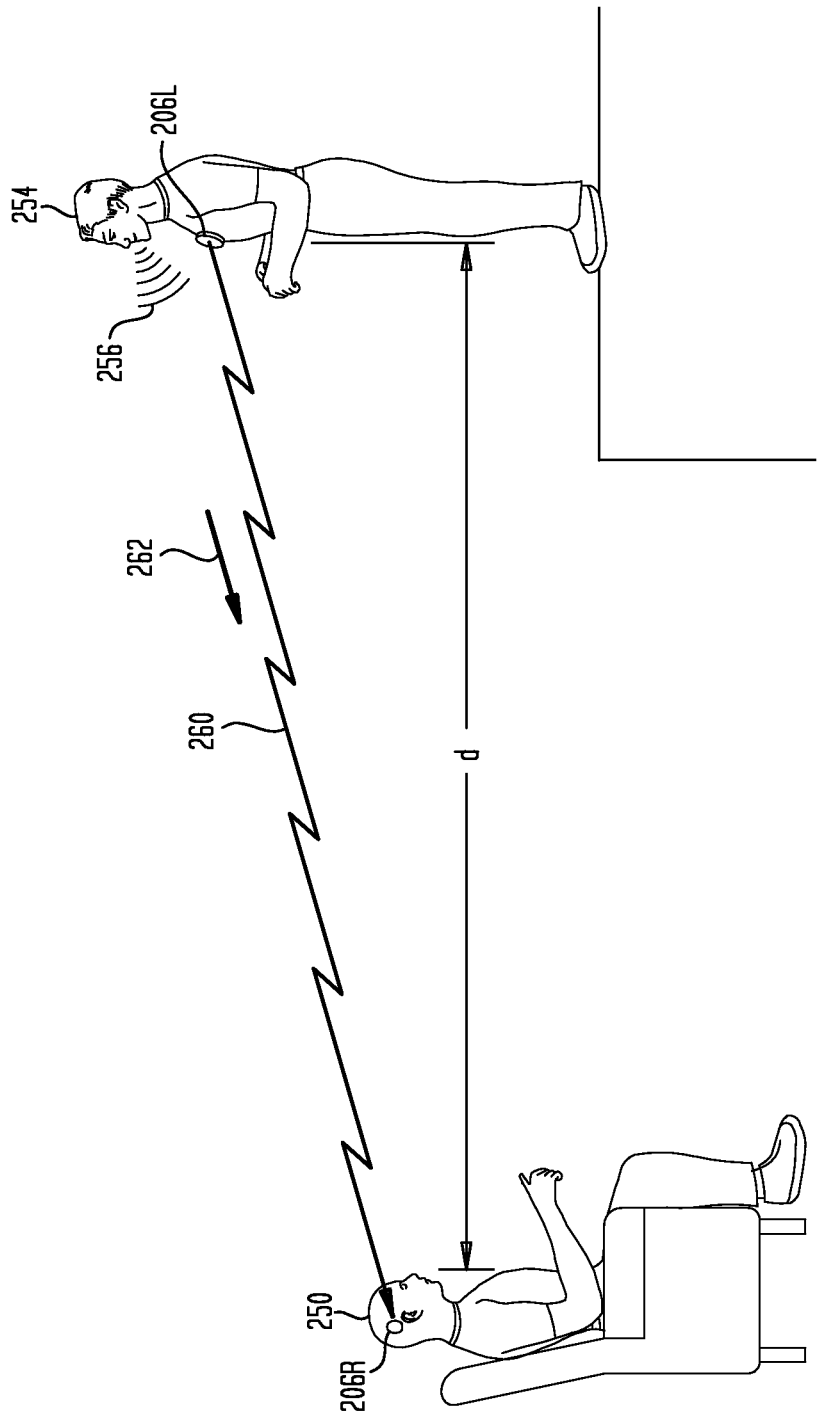

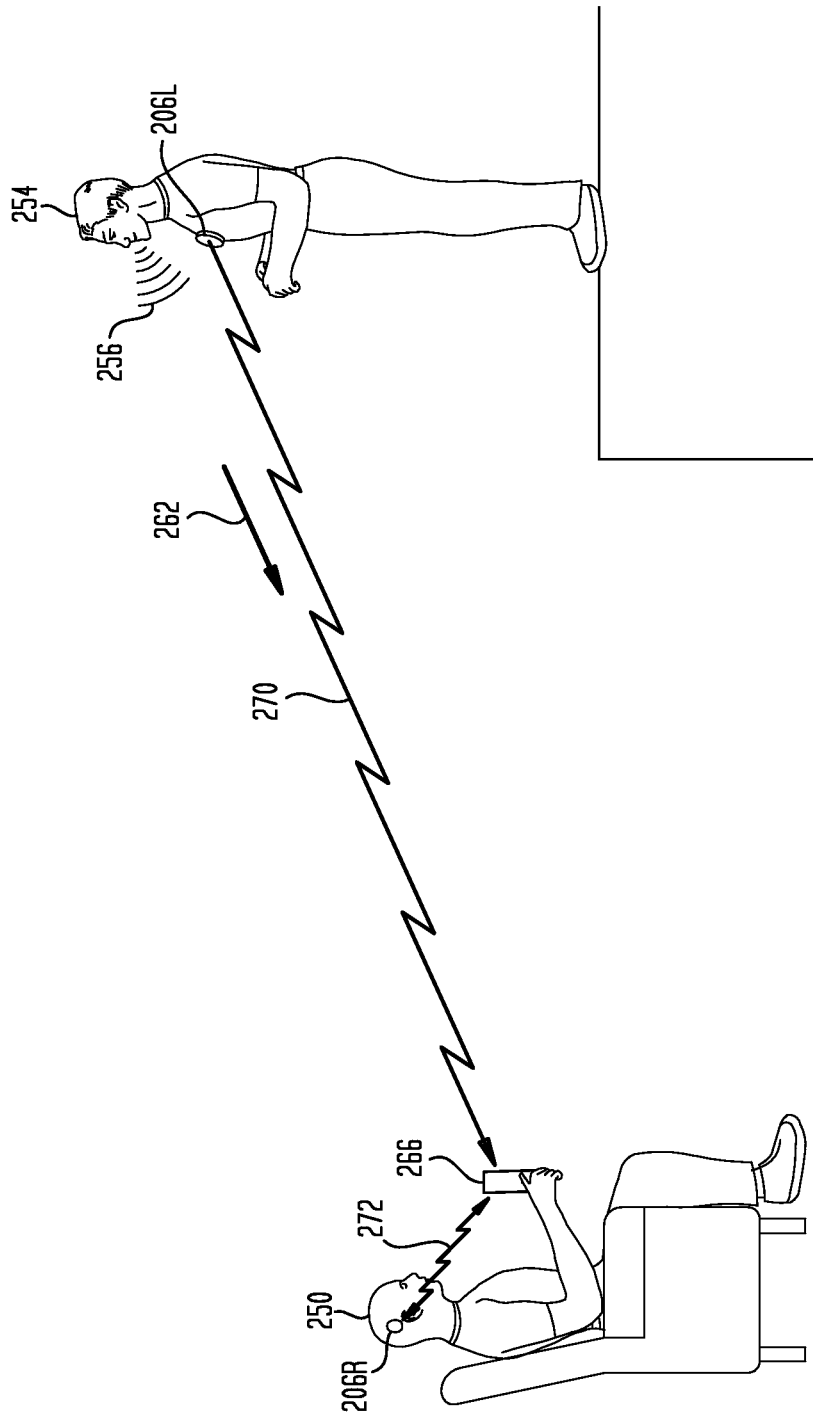

WIRELESS STREAMING SOUND PROCESSING UNIT

BACKGROUND

Field of the Invention

The present invention relates generally to hearing prosthesis sound processing units that are selectively operable to perform wireless streaming operations.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, to the nerve pathways from the inner ear to the brain, or the brain itself.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to, for example, damage to the auditory nerve.

Certain individuals suffer from only partial sensorineural hearing loss and, as such, retain at least some residual hearing. These individuals may be candidates for electro-acoustic hearing prostheses.

SUMMARY

In one aspect presented herein, a sound processing unit of a hearing prosthesis system is provided. The sound processing unit comprises: one or more input devices; a wireless transceiver; and one or more processors configured to: operate in a sound processing mode to convert input signals received at the one or more input devices into output signals for use in stimulating a first ear of a recipient, and selectively operate in a wireless streaming mode to encode input signals received at the one or more input devices into wireless transmission by the wireless transceiver.

In another aspect presented herein, a method is provided. The method comprises: receiving a first set of input signals at one or more input devices of a first sound processing unit; operating the first sound processing unit in a sound processing mode to convert the first set of input signals into output signals for use in stimulating a first ear of a recipient; detecting initiation of a wireless streaming mode at the first sound processing unit; receiving a second set of input signals at the one or more input devices of the first sound processing unit; and operating the first sound processing unit in a wireless streaming mode to encode the second set of input signals for wireless transmission.

In another aspect presented herein, a hearing prosthesis system is provided. The hearing prosthesis system comprises: a first implantable component; a first external sound processing unit configured for communication with the implantable component, wherein the first external sound processing unit comprises: one or more input devices; a wireless transceiver; and a dual-mode sound processing module configured to selectively perform sound processing operations or wireless streaming operations on input signals received at the one or more input devices.

BRIEF DESCRIPTION OF THE DRAWINGS

Embodiments of the present invention are described herein in conjunction with the accompanying drawings, in which:

FIG. 2B is a schematic diagram illustrating a wireless streaming mode of a sound processing unit, according to certain embodiments;

FIG. 2C is another schematic diagram illustrating a wireless streaming mode of a sound processing unit, according to certain embodiments;

DETAILED DESCRIPTION

Figure 1A:
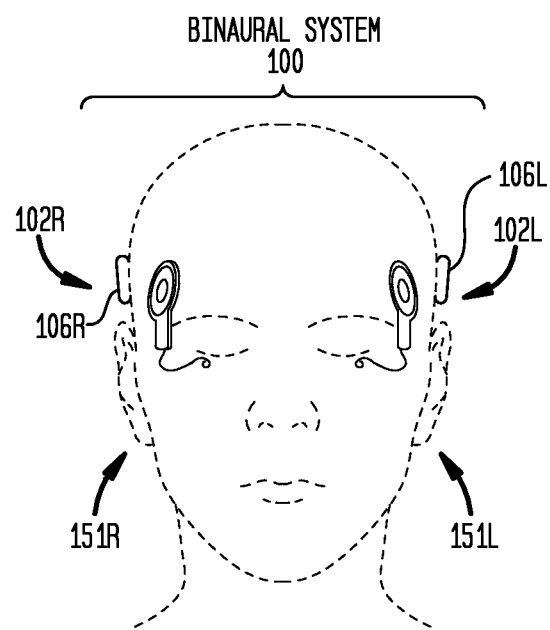
FIG. 1A is a schematic view of a binaural hearing prosthesis system in which embodiments presented herein may be implemented.

A binaural hearing prosthesis system includes two auditory/hearing prostheses that are each configured to convert sound signals into one or more of acoustic, mechanical, and/or electrical stimulation signals (collectively and generally "stimulation signals") for delivery to a recipient. The one or more hearing prostheses that can form part of a binaural hearing prosthesis system include, for example, hearing aids, cochlear implants, middle ear stimulators, bone conduction devices, brain stem implants, electro-acoustic devices, and other devices providing acoustic, mechanical, and/or electrical stimulation to a recipient. The various different types of hearing prostheses may also be used in a number of different combinations.

Hearing prosthesis recipients suffer from different types of hearing loss (e.g., conductive and/or sensorineural) and/or different degrees/severity of hearing loss. A particular hearing prosthesis recipient may also experience different types/degrees of hearing losses in each of his/her ears (i.e., sensorineural loss in the first ear, conductive hearing loss the second ear; severe sensorineural loss in the first ear, mild or moderate sensorineural loss in the second ear, or other various hearing loss combinations). As such, the various different types of hearing prostheses may also be used in a number of different combinations.

The effectiveness of binaural hearing prosthesis systems have improved dramatically and are effective in enabling recipients to perceive sounds in a number of different listening situations/environments. However, recipients may still encounter particularly challenging listening situations, such as certain noisy environments (e.g., restaurants), hearing over a distance (e.g., lecture halls, classrooms, presentations, panel discussions, etc.), etc. In such challenging listening situations, a recipient of a conventional hearing prosthesis system may have difficultly, for example, hearing speech, differentiating speakers, etc.

Conventional techniques attempt to assist a recipient in a challenging listening situation through the use of one or more so-called "wireless accessories" that operate with the hearing prostheses. In these conventional techniques, each wireless accessory is an electronic device (e.g., wireless microphone system, mobile device, smart watch, etc.) that is separate and discrete from the hearing prostheses. A wireless accessory is carried by a user (e.g., recipient, caregiver, etc.) and then strategically placed in order to capture additional sound inputs that are provided to the hearing prostheses worn by the recipient. The hearing prostheses then process the additional sound inputs provided by the wireless accessory, possibly along with sound inputs captured by the hearing prostheses themselves, for use in stimulating the recipient.

Although wireless accessories are used successfully by many recipients, their use also suffers from several drawbacks. In particular, since the wireless accessories are separate devices, they often must be purchased separately from the hearing prostheses. This increases the costs for the recipient and may limit accessibility to certain recipients. In addition, the separate nature of the wireless accessories requires the user to carry the wireless accessory with them so that the wireless accessory is available for use, when needed. The separate nature of the wireless accessories may also require the user to obtain additional service and learn to use additional software. The need to carry a separate device, as well as separate cables, chargers, etc., the need for additional service, the need for additional software, etc., may be deterrents to the use of wireless accessories and could be particularly inconvenient or unsuitable for young children, the elderly, or other recipients.

Presented herein are techniques to reduce or eliminate the need for the use of wireless accessories in binaural hearing prosthesis systems. More specifically, in accordance with the techniques presented herein, at least one of the first or second hearing prostheses of a binaural hearing prosthesis system includes a dual-mode sound processing unit that is configured to selectively operate in a "sound processing mode" or in a "wireless streaming mode." When operating in the sound processing mode, the dual-mode sound processing unit is configured to convert received sound signals into output signals for use in stimulating a first ear of a recipient. However, while operating in the wireless streaming mode, the dual-mode sound processing unit is configured to capture input signals (e.g., sound signals, data signals, etc.) and to encode those input signals for direct or indirect wireless (digital or analog) transmission to the sound processing unit of the other hearing prosthesis of the binaural hearing system. As described further below, the ability of the dual-mode sound processing unit to selectively operate in the wireless streaming mode provides the recipient with the functionality of a wireless accessory without the requirement to carry a separate device (i.e., the sound processing unit selectively functions as an integrated or always-with-you wireless accessory).

As noted above, embodiments presented herein are implemented by binaural hearing prosthesis systems. As used herein, a "binaural" hearing prosthesis system is a system that includes first and second hearing prostheses located at first and second ears, respectively, of a recipient. In such systems, each of the two hearing prostheses provides stimulation to one of the two ears of the recipient (i.e., either the right or the left ear of the recipient). The hearing prostheses in such systems may include, for example, hearing aids, cochlear implants, middle ear stimulators, bone conduction devices, brain stem implants, electro-acoustic devices, and other devices providing acoustic, mechanical, and/or electrical stimulation to a recipient. That is, in the binaural hearing prosthesis systems presented herein, the two hearing prostheses may be the same or different (e.g., two cochlear implants, a cochlear implant and a hearing aid, a cochlear implant and a bone conduction device, etc.).

Figure 1B:
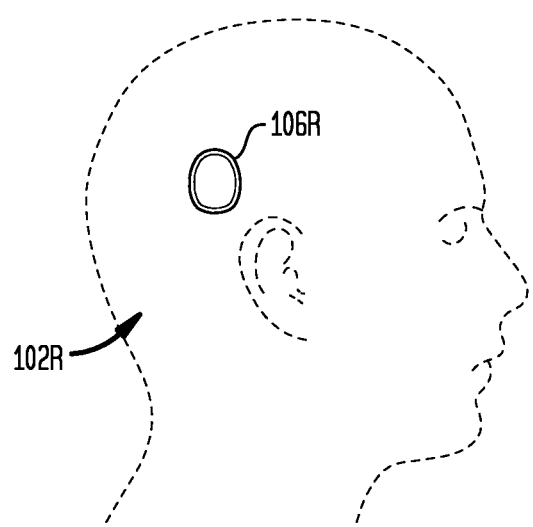
FIG. 1B is a side view of a recipient wearing the binaural hearing prosthesis system of FIG. 1A.
Figure 1C:
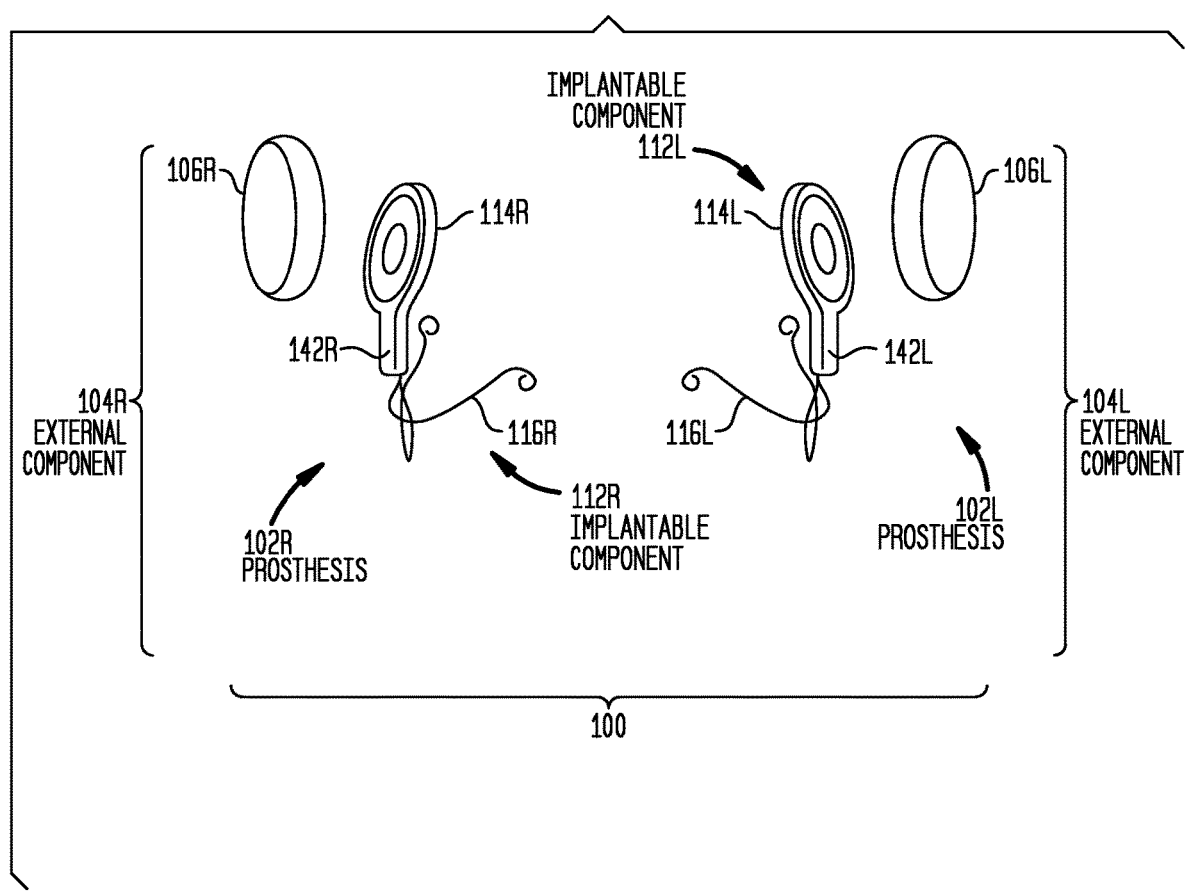
FIG. 1C is a schematic view of the components of the binaural hearing prosthesis system of FIG. 1A.
Figure 1D:
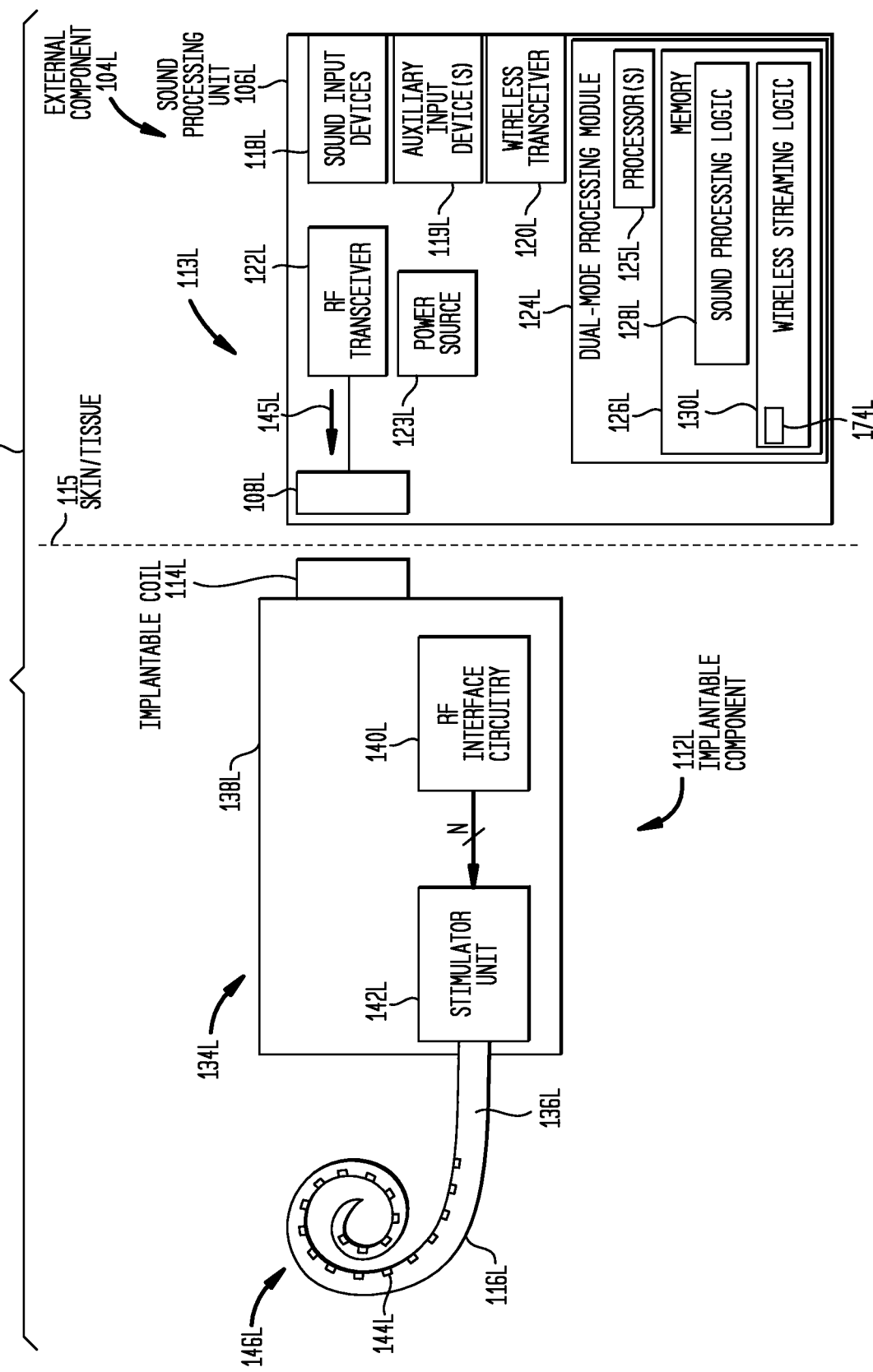
FIGS. 1D and 1E are block diagrams of sound processing units forming part of the binaural hearing prosthesis system of FIG. 1A.
Figure 1E:
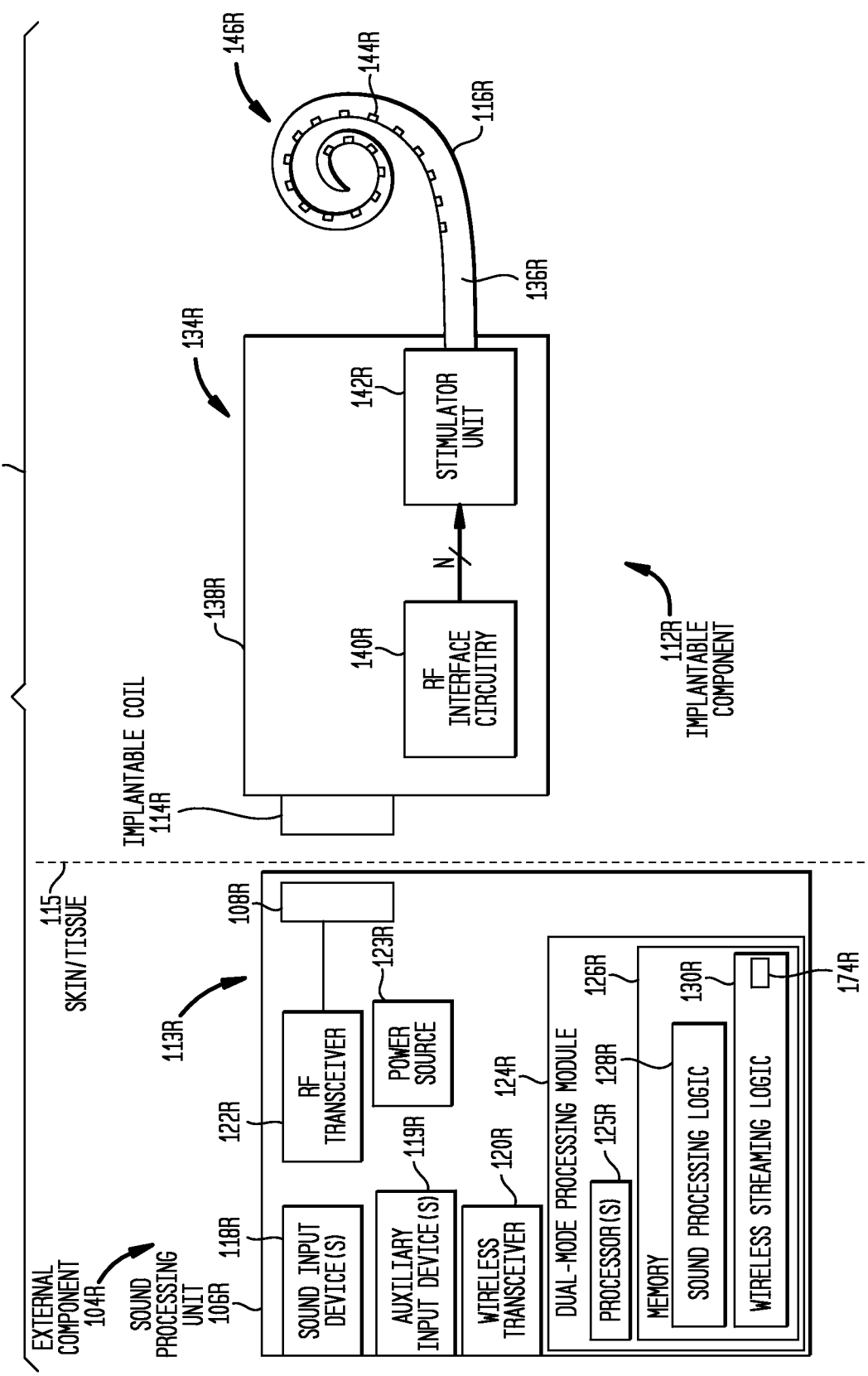

FIGS. 1A-1E are diagrams illustrating one example binaural hearing prosthesis system 100 configured to implement the techniques presented herein. More specifically, FIGS. 1A-1E illustrate an example binaural system 100 comprising left and right cochlear implants, referred to as cochlear implant 102L and cochlear implant 102R. FIGS. 1A and 1B are schematic drawings of a recipient wearing the left cochlear implant 102L at a left ear 151L and the right cochlear implant 102R at a right ear 151R, while FIG. 1C is a schematic view illustrating further details of each of the left and right cochlear implants. FIGS. 1D and 1E are block diagrams illustrating further details of the left cochlear implant 102L and the right cochlear implant 102R, respectively.

Referring specifically to FIG. 1C, cochlear implant 102L includes an external component 104L that is configured to be directly or indirectly attached to the body of the recipient and an implantable component 112L configured to be implanted in the recipient. The external component 104L comprises a sound processing unit 106L, while the implantable component 112L includes an internal coil 114L, a stimulator unit 142L and an elongate stimulating assembly (electrode array) 116L implanted in the recipient's left cochlea (not shown in FIG. 1C).

The cochlear implant 102R is substantially similar to cochlear implant 102L. In particular, cochlear implant 102R includes an external component 104R comprising a sound processing unit 106R, and an implantable component 112R comprising internal coil 114R, stimulator unit 142R, and elongate stimulating assembly 116R.

FIG. 1D is a block diagram illustrating further details of cochlear implant 102L, while FIG. 1E is a block diagram illustrating further details of cochlear implant 102R. As noted, cochlear implant 102R is substantially similar to cochlear implant 102L and includes like elements as that described below with reference to cochlear implant 102L. For ease of description, further details of cochlear implant 102R have been omitted from the description. Although these illustrative embodiments include two cochlear implants, it is to be appreciated that embodiments presented herein may be implemented in binaural hearing prosthesis systems that include other combination of prostheses, such as a cochlear implant at one ear and a hearing aid at the second ear, two electro-acoustic hearing prostheses, etc.

As noted, the external component 104L of cochlear implant 102L includes a sound processing unit 106L. The sound processing unit 106L comprises one or more input devices 113L that are configured to receive input signals (e.g., sound or data signals). In the example of FIG. 1D, the one or more input devices 113L include one or more sound input devices 118L (e.g., microphones, audio input ports, telecoils, etc.), one or more auxiliary input devices 119L (e.g., audio ports, such as a Direct Audio Input (DAI), data ports, such as a Universal Serial Bus (USB) port, cable port, etc.), and a wireless transmitter/receiver (transceiver) 120L. The sound processing unit 106L also comprises one type of a closely-coupled transmitter/receiver (transceiver) 122L, referred to as or radio-frequency (RF) transceiver 122L, a power source 123L, and a dual-mode processing module 124L. The dual-mode processing module 124L comprises one or more processors 125L and a memory 126L that includes sound processing logic 128L, and wireless streaming logic 130L that includes a codec 174L. In the examples of FIGS. 1A-1E, the sound processing unit 106L and the sound processing unit 106R are buttons sound processing units (i.e., components having a generally cylindrical shape and which is configured to be magnetically coupled to the recipient's head), etc. However, it is to be appreciated that embodiments of the present invention may be implemented by sound processing units having other arrangements, such as by a behind-the-ear (BTE) sound processing unit configured to be attached to and worn adjacent to the recipient's ear, including a mini or micro-BTE unit, an in-the-canal unit that is configured to be located in the recipient's ear canal, a body-worn sound processing unit, etc.

The implantable component 112L comprises an implant body (main module) 134L, a lead region 136L, and the intra-cochlear stimulating assembly 116L, all configured to be implanted under the skin/tissue (tissue) 115 of the recipient. The implant body 134L generally comprises a hermetically-sealed housing 138L in which RF interface circuitry 140L and a stimulator unit 142L are disposed. The implant body 134L also includes the internal/implantable coil 114L that is generally external to the housing 138L, but which is connected to the transceiver 140L via a hermetic feedthrough (not shown in FIG. 1D).

As noted, stimulating assembly 116L is configured to be at least partially implanted in the recipient's cochlea. Stimulating assembly 116L includes a plurality of longitudinally spaced intra-cochlear electrical stimulating contacts (electrodes) 144L that collectively form a contact or electrode array 146L for delivery of electrical stimulation (current) to the recipient's cochlea.

Stimulating assembly 116L extends through an opening in the recipient's cochlea (e.g., cochleostomy, the round window, etc.) and has a proximal end connected to stimulator unit 142L via lead region 136L and a hermetic feedthrough (not shown in FIG. 1D). Lead region 136L includes a plurality of conductors (wires) that electrically couple the electrodes 144L to the stimulator unit 142L.

As noted, the cochlear implant 102L includes the external coil 108L and the implantable coil 114L. The coils 108L and 114L are typically wire antenna coils each comprised of multiple turns of electrically insulated single-strand or multi-strand platinum or gold wire. Generally, a magnet is fixed relative to each of the external coil 108L and the implantable coil 114L. The magnets fixed relative to the external coil 108L and the implantable coil 114L facilitate the operational alignment of the external coil 108L with the implantable coil 114L. This operational alignment of the coils enables the external component 104L to transmit data, as well as possibly power, to the implantable component 112L via a closely-coupled wireless link formed between the external coil 108L with the implantable coil 114L. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1D illustrates only one example arrangement.

As noted above, sound processing unit 206L includes the dual-mode processing module 124L. The dual-mode processing module 124L is configured to selectively operate in two primary manners (modes), namely in a "sound processing mode" or in a "wireless streaming mode." When operating in the sound processing mode, the dual-mode processing module 124L is configured to convert received input signals into output signals 145L for use in stimulating a first ear of a recipient (i.e., the dual-mode processing module 124L is configured to perform sound processing on input signals received at the sound processing unit 106L). Stated differently, in the sound processing mode, the one or more processors 125L are configured to execute sound processing logic 128L in memory 126L to convert the received input signals into output signals 145L that represent electrical stimulation for delivery to the recipient. The input signals that are processed and converted into output signals may be signals received via the sound input devices 118L, signals received via the auxilliary input devices 119L, and/or signals received via the wireless transceiver 120L.

In the embodiment of FIG. 1D, the output signals 145L are provided to the RF transceiver 114, which transcutaneously transfers the output signals 145L (e.g., in an encoded manner) to the implantable component 112L via external coil 108L and implantable coil 114L. That is, the output signals 145L are received at the RF interface circuitry 140L via implantable coil 114L and provided to the stimulator unit 142L. The stimulator unit 142L is configured to utilize the output signals 145L to generate electrical stimulation signals (e.g., current signals) for delivery to the recipient's cochlea via one or more stimulating contacts 144L. In this way, cochlear implant 102L electrically stimulates the recipient's auditory nerve cells, bypassing absent or defective hair cells that normally transduce acoustic vibrations into neural activity, in a manner that causes the recipient to perceive one or more components of the received sound signals.

When in the sound processing mode, the one or more processors 125L (executing sound processing logic 128L) generate output signals 145L in accordance with various operating parameters/settings. The various operating parameters may be in the form of executable programs or sets of parameters for use in a program and form part of sound processing logic 128L. The settings may accommodate any of a number of specific configurations that influence the operation of the cochlear implant 102L. For example, the operating parameters may include different digital signal and sound processing algorithms, processes and/or operational parameters for different algorithms, other types of executable programs (such as system configuration, user interface, etc.), or operational parameters for such programs. The operating parameters may also include different optimal settings for different listening situations or environments encountered by the recipient (i.e., noisy or quite environments, windy environments, or other uncontrolled noise environments).

Additionally, since the dynamic range for electrical stimulation is relatively narrow and varies across recipients and stimulating contacts, parameters used in sound processing are typically individually tailored to optimize the perceptions presented to a particular recipient (i.e., tailor the characteristics of electrical stimulation for each recipient). For example, many speech processing strategies rely on a customized set of stimulation settings which provide, for a particular recipient, the threshold levels (T-levels) and comfortable levels (C-levels) of stimulation for each frequency band. Once these stimulation settings are established, the processor(s) may then optimally process and convert the received sound signals into output signals for use in delivering electrical or acoustical stimulation signals to the recipient.

As such, it is clear that a typical cochlear implant, or other types of hearing prostheses, have many parameters which determine the sound processing operations of the device. The individualized programs, commands, data, settings, parameters, instructions, and/or other information that define the specific characteristics used by a hearing prosthesis to process input signals and generate stimulation data therefrom are generally and collectively referred to as "sound processing settings."

As noted above, in addition to the sound processing mode, the dual-mode processing module 124L (and thus the sound processing unit 106L) may also operate in a wireless streaming mode. When in the wireless streaming mode, the dual-mode sound processing module 124L is configured to capture input signals (e.g., sound or data signals) and to encode those input signals for direct or indirect wireless transmission to the sound processing unit 106R of cochlear implant 102R of the binaural hearing system. Further details of the wireless streaming mode are provided below with reference to FIGS. 2B, 2C, 3, 4A, and 4B.

In summary, while the dual-mode processing module 124L is in the sound processing mode, the sound processing unit 106L is configured to operate in accordance with the determined sound processing settings (e.g., the individualized programs, commands, data, settings, parameters, instructions, etc.) to convert received sound/audio signals into electrical stimulation that is delivered to the recipient. The sound processing mode is the primary/default mode for the sound processing unit 106L. However, while the dual-mode processing module 124L is in the wireless streaming mode, the sound processing unit 106L is configured to capture input signals (e.g., sound or data signals) and to encode those input signals for direct or indirect wireless transmission to the sound processing unit 106R of cochlear implant 102R of the binaural hearing system. Due to these different modes, the sound processing unit 106L is sometimes referred to herein as a "dual-mode sound processing unit" that can operate in a sound processing mode or in a wireless streaming mode.

As noted, cochlear implant 102R is substantially similar to cochlear implant 102L and comprises external component 104R and implantable component 112R. External component 104R includes a sound processing unit 106R that comprises external coil 108R, input devices 113R (i.e., one or more sound input devices 118R, one or more auxiliary input devices 119R, and wireless transceiver 120R), closely-coupled transceiver (RF transceiver) 122R, power source 123R, and dual-mode processing module 124R. The dual-mode processing module 124R includes one or more processors 125R and a memory 126R that includes sound processing logic 128R and wireless streaming logic 130R that includes a codec 174R. The implantable component 112R includes an implant body (main module) 134R, a lead region 136R, and the intra-cochlear stimulating assembly 116R, all configured to be implanted under the skin/tissue (tissue) 115 of the recipient. The implant body 134R generally comprises a hermetically-sealed housing 138R in which RF interface circuitry 140L and a stimulator unit 142R are disposed. The implant body 134R also includes the internal/implantable coil 114R that is generally external to the housing 138R, but which is connected to the RF interface circuitry 140R via a hermetic feedthrough (not shown in FIG. 1E). The stimulating assembly 116R includes a plurality of longitudinally spaced intra-cochlear electrical stimulating contacts (electrodes) 144R that collectively form a contact or electrode array 146R for delivery of electrical stimulation (current) to the recipient's cochlea. Each of the elements of cochlear implant 102R shown in FIG. 1E are similar to like-numbered elements of cochlear implant 102L shown in FIG. 1D.

FIGS. 1A-1E illustrate arrangements in which the cochlear implants 102L and 102R are substantially similar to one another and each include a dual-mode sound processing unit (i.e., sound processing units 106L and 106R are each configured to operate in a sound processing mode or in a wireless streaming mode). It is to be appreciated that these specific embodiments are illustrative and of the present invention may be implemented in binaural hearing prosthesis systems that include one dual-mode sound processing unit and a conventional sound processing unit with a wireless receiver (or transceiver) configured to receive the wireless signals streamed by the dual-mode sound processing unit, as described further below. As such, the arrangements of FIGS. 1A-1E are illustrative of one of many arrangements in which embodiments presented herein may be implemented.

Figure 2A:
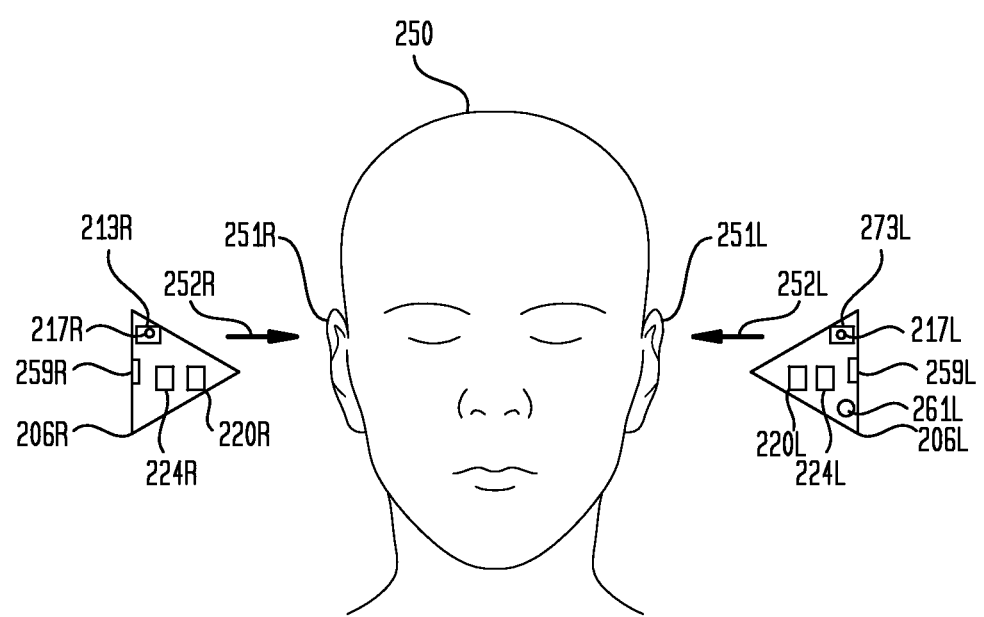
FIG. 2A is a schematic diagram illustrating a sound processing mode of a sound processing units, according to certain embodiments.

As noted above, a dual-mode sound processing unit of a binaural hearing prosthesis system in accordance with embodiments presented herein is configured to selectively operate in a sound processing mode or a wireless streaming mode. FIG. 2A is a schematic diagram illustrating operation a dual-mode sound processing unit in a sound processing mode, while FIGS. 2B and 2C are schematic diagrams illustrating operation of a dual-mode sound processing unit in two illustrative wireless streaming modes.

Referring first to FIG. 2A, shown is a binaural hearing prosthesis system 200 that includes a first sound processing unit 206L and second sound processing unit 206R that are each worn by a recipient 250. For ease of description, the sound processing units 206L and 206R are each part of a cochlear implant and are each substantially similar to sound processing units 106L and 106R described above with reference to FIGS. 1A-1E. As such, also for ease of description, the details of the sound processing units 206L and 206R have been omitted from FIG. 2. The recipient 250 includes a left ear 251L (including outer, middle, and inner ear) and a right ear 251R (again including outer, middle, and inner ear).

In the example of FIG. 2A, both of the sound processing units 206L and 206R operate to receive sound signals via one or more respective input devices 213L, 213R. As described further below, the input devices 213L include a microphone array 217L formed by one or more microphones, and at least a wireless transceiver 220L. The input devices 213R include a microphone array 217R formed by one or more microphones, and at least a wireless transceiver 220R. The sound processing units 206L and 206R also include respective user interfaces 259L and 259R, as well as respective dual-mode processing modules 224L, 224R. The dual-mode processing modules 224L and 224R operate to convert the received input signals into output signals 252L and 252R, respectively, for use in stimulating the recipient. In particular, the output signals 252L and 252R are transmitted to respective implantable components (not shown in FIG. 2) and used to generate electrical stimulation for delivery to the respective ear 251L or 251R.

Referring next to FIG. 2B, shown is a schematic diagram in which the sound processing unit 206L is removed from the head of the recipient 250 and is configured to operate in a wireless streaming mode. In the example of FIG. 2B, the recipient 250 is positioned a distance (d) from a speaker 254 in, for example, a classroom or lecture environment. Given the distance d, if the sound processing units 206L and 206R were both worn by the recipient 250, the sound processing units 206L and 206R could have difficulty capturing and properly representing speech signals 256 of the speaker 254. As such, in accordance with embodiments of the present invention, the sound processing unit 206L is removed from the head of the recipient 250 and placed in relative proximity to the speaker 254 (i.e., within a predetermined distance from the speaker).

When the sound processing unit 206L is removed from the head of the recipient 250, the sound processing unit 206L is configured to operate in the wireless streaming mode (i.e., the wireless streaming mode of the dual-mode processing module 224L is initiated/activated). As described further below, the wireless streaming mode may be initiated manually by the recipient or the wireless streaming mode may be initiated/activated automatically based on the detection of one or more triggering conditions.

Once the wireless streaming mode is activated, the sound processing unit 206L (more specifically the dual-mode processing module 224L) no longer operates to convert detected input signals into output signals for transmission to an implantable component. Instead, when in the wireless streaming mode, the dual-mode processing module 224L operates to encode received input signals (e.g., speech signals 256 of the speaker 254) for wireless transmission to the sound processing unit 206R via a wireless channel 260. That is, as described further below, when in the wireless streaming mode, the dual-mode processing module 224L is configured to encode the input signals (or a processed version thereof) for wireless transmission on the wireless channel 260.

In certain embodiment embodiments, the wireless channel 260 may be a digital wireless channel and the dual-mode processing module 224L may implement a digital encoding scheme to encode the input signals (or a processed version thereof) for wireless transmission on the wireless channel 260. In other embodiments, the wireless channel 260 may be an analog wireless channel and the dual-mode processing module 224L may implement an analog encoding scheme to encode the input signals (or a processed version thereof) for wireless transmission on the wireless channel 260. Merely for ease of illustration, embodiments of the present invention are primarily described with reference to an example digital encoding scheme. As noted, it is to be appreciated that these digital encoding embodiments are illustrative and that analog encoding schemes may be used in other embodiments of the present invention.

In the digital encoding example of FIG. 2B, to encode the encode the input signals (or a processed version thereof) for wireless transmission on the wireless channel 260, the dual-mode processing module 224L is configured to activate a codec 274L (FIG. 4A) that is specifically designed and configured to encode or otherwise adapt the input signals (or a processed version thereof) to a packet/frame format, packet length, and packet rate made available by a wireless transport interface (i.e., available on the wireless channel 260). In other words, the activated codec 274L in the dual-mode processing module 224L identifies the wireless packet/frame format for the wireless channel 260 and then encodes or maps the input signals (or a processed version thereof) into the available packet format. The wireless transceiver 220R then transmits/sends the wireless packets 262 to the sound processing unit 206R, which is worn by the recipient.

In certain examples, the wireless channel 260 of FIG. 2B may be a standardized wireless channel, such as Bluetooth®, Bluetooth® Low Energy (BLE) or other channel interface making use of any number of standard wireless streaming protocols. Bluetooth® is a registered trademark owned by the Bluetooth® SIG. In other examples, the wireless channel 260 of FIG. 2B may be a proprietary channel that makes use of a proprietary protocol for wireless streaming of the input signals.

As noted, and as described further below, the sound processing unit 206L may be configured to wirelessly stream the input signals received at the input devices 213L, or a processed version of the input signals, to the sound processing unit 206R. The input signals and processed versions of the input signals are collectively and generally referred to herein as "input data."

Figure 3:
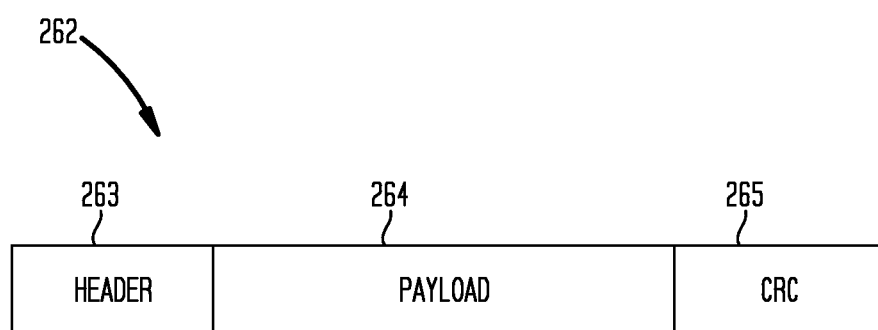
FIG. 3 is a block diagram of an example wireless packet, according to certain embodiments.

FIG. 3 is a schematic diagram illustrating one example format for wireless packet 262 into which input data (i.e., the input signals received at the input devices 213L or a processed version of the input signals) may be encoded/mapped in accordance with the example of FIG. 2B (i.e., a wireless packet sent via wireless channel 260). In FIG. 3 the wireless packet 262 comprises a header 263, a payload 264 of the input data, and an error correction field/trailer 265. The payload 266 may include 8 bits, 16 bits, 32 bits, etc. of formatted data, which is comprised of the encoded input data (i.e., the input signals or a processed version thereof). The error correction field 268 may include Cyclic Redundancy Check (CRC) information. It is to be appreciated that, since the payload 266 is generated based on the input signals received at the input devices 213, the size of the payload may vary from packet to packet on the wireless channel 260. It is also to be appreciated that the packet format of FIG. 3 is illustrative and that a sound processing unit in accordance with embodiments presented herein may use different packet formats to send the encoded wireless signals.

As noted above, FIG. 2B illustrates an example in which a wireless channel 260 is formed between the sound processing units 206L and 206R. It is to be appreciated that this arrangement is illustrative and that, in certain embodiments, the sound processing unit 206L may be configured to instead wirelessly stream the wireless packets to an external (intermediate) device 266, such as a mobile phone, remote control, etc., which is then configured to forward the wireless packets, or the input data, to the sound processing unit 206R. An example of such an arrangement is shown in FIG. 2C.

More specifically, FIG. 2C illustrates that a first wireless communication channel 270 is formed between the sound processing unit 206L and the external device 266, and that a second wireless communication channel 272 is formed between the external device 266 and the sound processing unit 206R. In these embodiments, the external device 266 receives wireless packets 262 that include the input data (i.e., the input signals received at sound processing unit 206L or a processed version thereof). The external device 266 is configure to perform one or more operations based on the received wireless packets 262. For example, in certain embodiments, the external device 266 operates as a relay device (e.g., modem) that forwards the wireless packets to sound processing unit 206R (e.g., via wireless transceiver 220R). In such embodiments, the wireless channel 272 may utilize the same communication protocols as wireless channel 270.

Although FIG. 2A illustrates an embodiment in which the sound processing unit 206R includes a wireless transceiver 220R, it is to be appreciated that this may not be the case for other sound processing units. That is, certain sound processing unit may lack the ability to communicate over a non-closely coupled wireless link. In such embodiments in which the sound processing unit worn by the recipient does not include the wireless transceiver 220R, the external device 266 may be configured to extract the input data from the wireless packets received via channel 270 and re-format the data for transmission via a different communication interface, such as a closely-coupled or near-field communication link (e.g., RF transmission at approximately 5 Megahertz (MHz), at approximately 6.78 MHz, at approximately 13.56 MHz, at approximately 27.12 MHz, etc.).

As noted, a dual-mode sound processing unit in accordance with embodiments presented herein, such as dual-mode sound processing unit 206L, can be configured to operate in the wireless streaming mode to directly or indirectly wirelessly stream input data to another sound processing unit. However, the wireless streaming mode is a selectively activated mode of the sound processing unit. In accordance with embodiments presented herein, the wireless streaming mode may be activated in a number of different manners.

In one embodiment, the wireless streaming mode is activated or deactivated via the user interface 259L (e.g., one or more buttons, a touch screen, etc.) of the sound processing unit 206L. In other embodiments, the wireless streaming mode is activated or deactivated via a user interface of an external device, such as external device 266, that is in communication with the sound processing unit 206L (e.g., in response to one or more user inputs, the external device 266 sends signals to the sound processing unit 206L to switch operation from the sound processing mode to the wireless streaming mode).

In other embodiments, the wireless streaming mode of sound processing unit 206L may be automatically activated or deactivated by the sound processing unit 206L itself, or the sound processing unit 206R, in response to detection of one or more triggering conditions. For example, the sound processing unit 206L may include an accelerometer 261L and a triggering condition is the detection, by the accelerometer 261L, of one or more of a predetermined orientation, predetermined motion pattern, etc. of the sound processing unit 206L. That is, a specific motion pattern, orientation, etc. could be detected by the accelerometer 261L, which in turn generates a signal that is provided to the dual-mode processing module 224L. The dual-mode processing module 224L could then initiate the wireless streaming mode when a signal indicated detection specific motion pattern, orientation, etc. is received from the accelerometer 261L.

As noted above, sound processing units (e.g., the sound processing unit 206L and sound processing unit 206R) in accordance with embodiments presented herein may include a coil that is configured to be inductively coupled to an implantable component. The sound processing units may also be configured to communicate with one another either directly or via an external device (e.g., using the external device as a wireless relay/router device). In certain such embodiments, the one or more triggering conditions that result in activation of the wireless streaming mode includes a detection of loss of coupling between the coil in a first processing unit and the associated implantable component, along with receipt of predetermined data from the second (contralateral) sound processing unit. The predetermined data from the from the second sound processing unit may be data indicating that the second sound processing unit is still worn by the recipient. Such a condition (i.e., where the first sound processing unit has been detached from the implantable component and the second processing unit remains worn by the recipient), could indicate that the removed/detached sound processing unit should activate the wireless streaming mode, rather than simply turn off, as in the case when the detached sound processing unit is being charged, manually deactivated, etc.

The specifics of the wireless streaming operations performed by the sound processing unit 206L while in the wireless streaming mode may vary and may also be set/determined in a number of different manners. In one embodiment, the wireless streaming operations are dynamically set by the sound processing unit 206L itself or dynamically set by the recipient, caregiver, or other user. In other embodiments, the wireless streaming operations are predetermined (e.g., by the device manufacturer, clinician, etc.).

As described in greater detail elsewhere herein, when in the wireless streaming mode the sound processing unit 206L is configured to wirelessly stream input data (directly or indirectly) to the sound processing unit 206R that remains worn by the recipient. However, in addition, the sound processing unit 206L can also be configured to perform one or more other operations. For example, in one embodiment, the sound processing unit 206L can deactivate all sound processing operations that are not used for wirelessly streaming input data.

In another embodiment, the sound processing unit 206L may adjust operation of the user interface 259L (e.g., displays, buttons, etc.) when the wireless streaming mode is activated. For example, the user interface 259L could include one or more light emitting diodes (LEDs). When in the sound processing mode, these LEDs may be activated to convey information to the recipient or other user (e.g., a blinking LED indicates the sound processing unit is coupled to the implant, an LED is illuminated to indicate an issue with the sound processing unit or implant, etc.). However, when in the wireless streaming mode, the sound processing unit 206L could be, for example, worn by a speaker, located on a table, sitting in front of a classroom, etc., where the LEDs could be distracting to the recipient or others. As such, the sound processing unit 206L could disable the LEDs when in the sound processing mode. The sound processing unit 206L could also or alternatively adjust change the functionality associated with any buttons when operating in the sound processing mode. For example, the functionality associated with buttons could be modified for use in the wireless streaming mode to repeat/refresh/confirm pairing, turn the wireless mode on/off, mute the input devices, etc.

In other embodiments, the physical arrangement of the sound processing unit 206L could be adjusted when in the wireless streaming mode. For example, in the case of a BTE, a recipient or other user could remove/omit attachments such as a coil, acoustic receiver, earhook, etc.

As noted, the input devices 213L of the sound processing unit 206L may include one or more microphones forming a microphone array 217L. The microphone array 217 could have an adjusted directionality when the sound processing unit is in the wireless streaming mode. For example, the one or more microphones could be optimized for omnidirectional operation when in the sound processing mode. However, when the sound processing unit 206L is in the wireless streaming mode, the one or more microphones could be enabled for beamforming or are otherwise optimized for one or more off-the-body positions. The directionality of the microphone array 217L could change based on how sound processing unit 206L is oriented, the source of the input signals, etc.

As noted elsewhere herein, the sound processing unit 206L wirelessly streams input data (directly or indirectly) to the sound processing unit 206R. In certain embodiments, no changes occur at the sound processing unit 206R and the sound processing unit 206R processes the wirelessly received input data in a manner that is similar to input signals received via any other input devices. In such examples, the sound processing unit 206R may mix the wirelessly streamed input data with input signals received at any other input devices in accordance with a mixing ratio. The mixing ratio may be predetermined (e.g., by a clinician) or could be dynamically adjustable by the recipient or the sound processing unit 206R itself.

As noted above, sound processing units 206L and 206R may be configured to communicate with one another either directly or via an external device. In such embodiments, the detached sound processing unit 206L may instruct the remaining sound processing unit 206R to make one or more operational adjustments to enhance the wireless streaming operations. For example, the detached sound processing unit 206L may instruct the remaining sound processing unit 206R to adjust the mixing ratio to emphasize the wirelessly streamed input data. In another example, the detached sound processing unit 206L may instruct the remaining sound processing unit 206R to change the sound coding behaviors (e.g., switch off all binaural features, perform gain adjustments, adjust beamformer characteristics of the microphone array 2178, etc.) to account for only one processing unit being worn by the recipient.

As noted, FIGS. 2B and 2C illustrate two examples in which the sound processing unit 206L is configured to wirelessly stream input signals to the sound processing unit 206R. In particular, FIG. 2B illustrates an arrangement in which the input signals are directly streamed to the sound processing unit 206R, while FIG. 2C illustrates an arrangement in which the input signals are indirectly streamed to the sound processing unit 206R via an external device 266. The selection of direct or indirect streaming may be based, for example, on the capabilities of the devices, relative distance, etc. With direct streaming, no additional device is needed, no further pairing is needed, thereby providing an easier experience. Indirect streaming may provide longer autonomy (bigger battery), a longer wireless range, no effect of head shadow, etc.

Figure 4A:
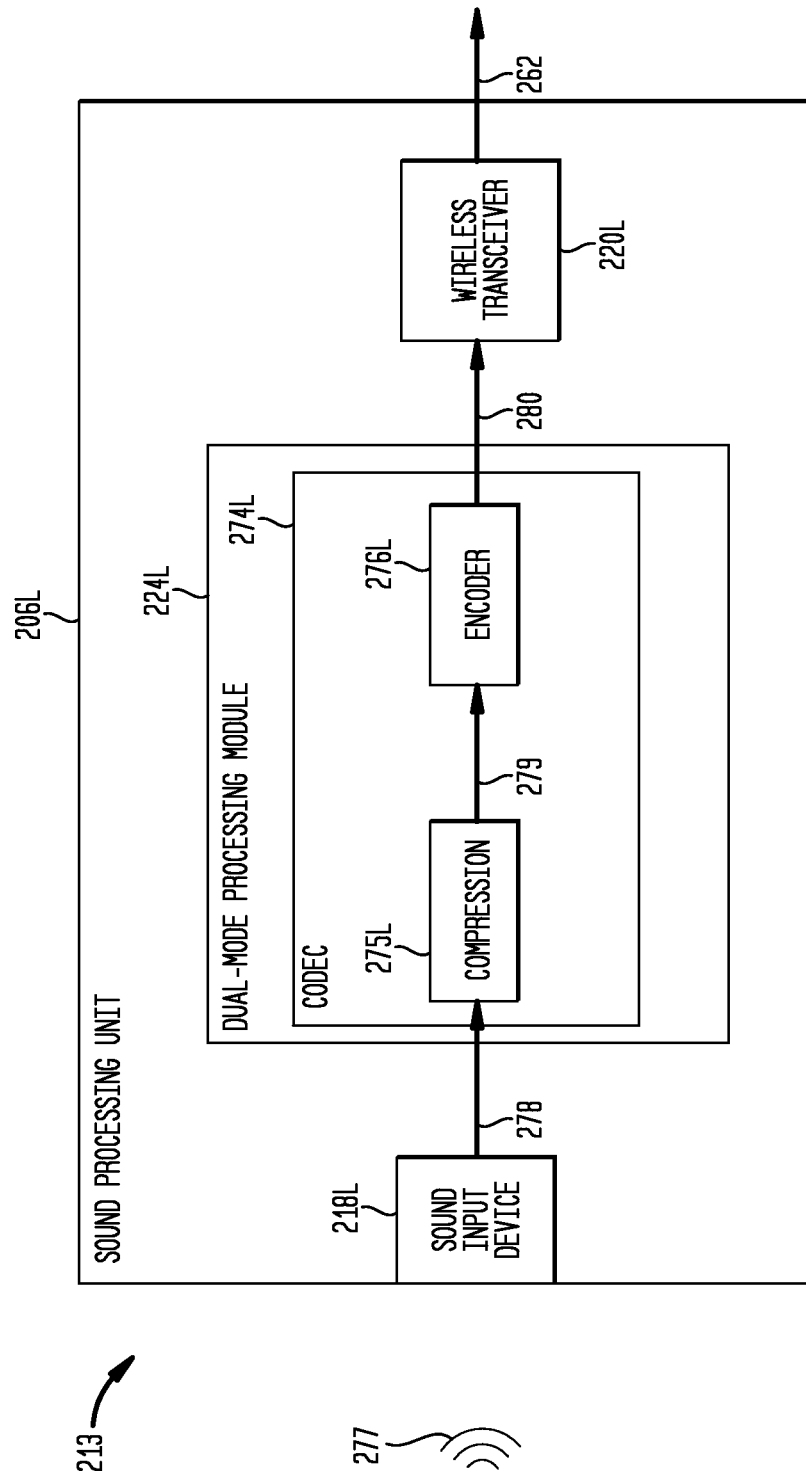
FIG. 4A is a functional block diagram of a sound processing unit in a wireless streaming mode, according to certain embodiments.

FIG. 4A is a functional block diagram illustrating elements of the dual-processing module 224L when operating in the wireless streaming mode in accordance with embodiments presented herein. In general, FIG. 4A illustrates only the elements of the dual-processing module 224L and sound processing unit 206L related to the streaming of the input data over a wireless channel in accordance with embodiments presented herein. For ease of illustration, other elements of the dual-processing module 224L and the sound processing unit 106L have been omitted from FIG. 4A.

Shown in FIG. 4A is one specific input device, namely a microphone 218L, the dual-processing module 224L, and the wireless transceiver 220L. The dual-processing module 224L includes a codec 274L that comprises a compression module 275L and an encoder 276L. In this embodiment, the microphone 218L is configured to receive/detect sound signals 277 and to convert the sound signals 277 into electrical input signals 278. The electrical input signals 278 are provided to the compression module 275L for compression. The compression module 275L generates compressed input data 279 which is then provided to the encoder 276L. The encoder 276L is configured to encode the compressed input data 279 for transmission within the selected wireless framework (i.e., packet/frame format) provided for the wireless channel (e.g., wireless channel 260 or 270). The encoded and compressed input data, generally represented in FIG. 4A by arrow 280, is then transmitted by the wireless transceiver 220L (i.e., the wireless transceiver 220L comprises the hardware/software to transmit the wireless packets 262). Although FIG. 4A illustrates the presence of compression module 275L, it is to be appreciated that in other embodiments the compression module 275L (and thus the compression operations) may be omitted.

As noted, the wireless packets 262 are transmitted either directly or indirectly to the sound processing unit 206R. As such, the sound processing unit 206R and/or the external device 266 is operable to decode the wireless packets 262 and extract the input data thereof.

FIG. 4A illustrates an arrangement in which the input signals (i.e., sound signal 277) are directly encoded for wireless transmission to the sound processing unit 206L (i.e., the input data generally corresponds to the input signals). However, in other embodiments, the input signals may be processed before being encoded for wireless transmission. Such an arrangement is shown in FIG. 4B.

Figure 4B:
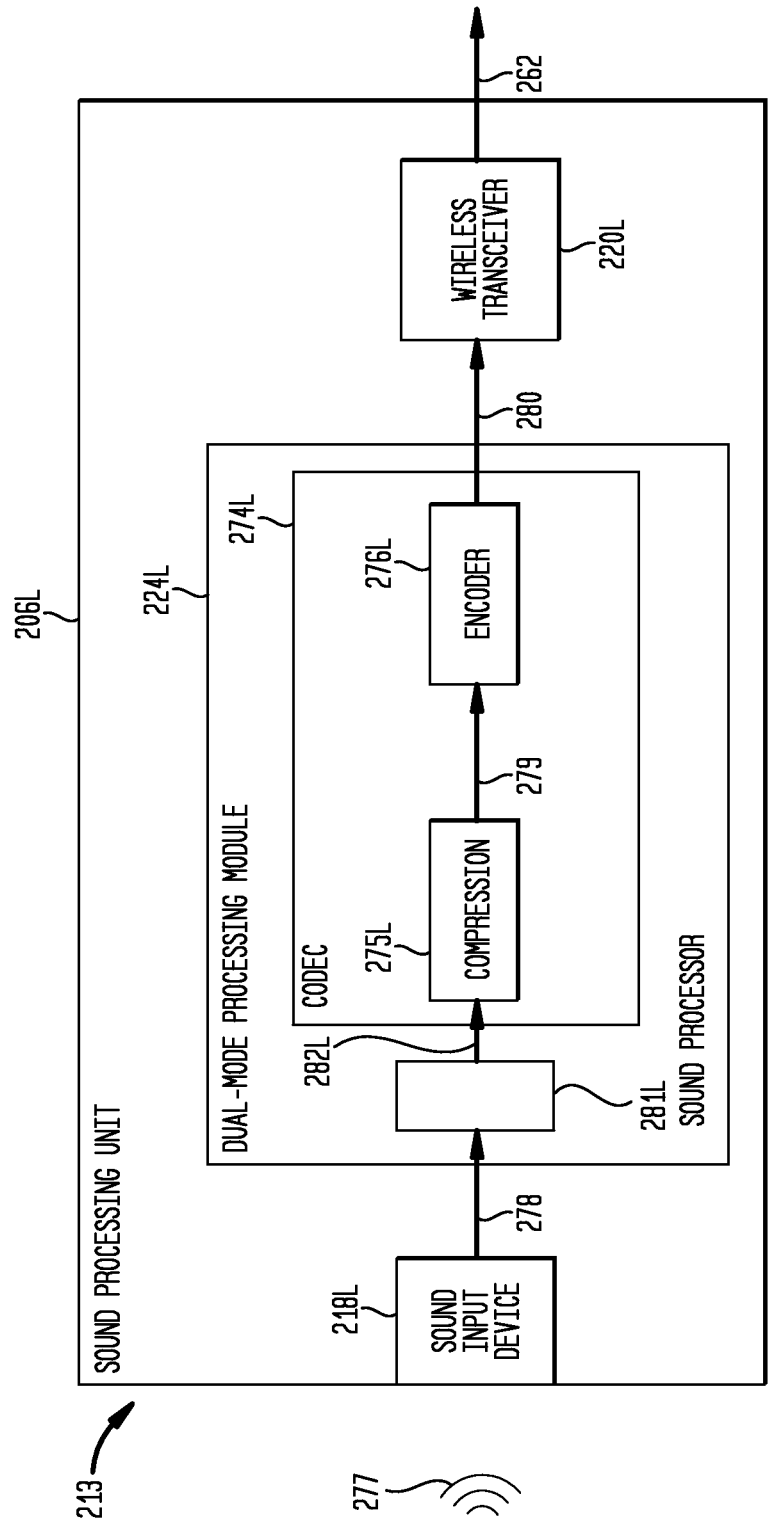
FIG. 4B is a functional block diagram of a sound processing unit in a wireless streaming mode, according to certain embodiments.

More specifically, FIG. 4B illustrates an arrangement similar to that of FIG. 4A, but in which the dual-mode processing module 224L also include a sound processor 218L (i.e., one or more processing execute sound processing software/logic). In these embodiments, the electrical input signals 278 are provided to the sound processor 281L. The sound processor 281L executes one or more sound processing/coding strategies to convert the electrical input signals 278 into processed input signals 282L. The processing input signals 282L are provided to the compression module 275L for generation of the compressed input data 279. Similar to the example of FIG. 4A, the encoder 276L is then configured to encode the compressed input data 279 for transmission via a wireless channel, such as wireless channel 260 or 270, via the wireless transceiver 220L. In the embodiments of FIG. 4B, the input data wirelessly streamed to the sound processing unit 206R is a sound processed version of the input signals, rather than generally the input signals themselves. As such, FIGS. 4A and 4B collectively illustrate that the wireless streamed input data can be full format or pre-processed audio (e.g., a mono stream which is lower in bandwidth and energy consumption).

FIGS. 4A and 4B illustrate arrangements in which sound signals received at a microphone 218L are used to generate input data that is wirelessly streamed to the sound processing unit 206R (either directly or indirectly). As noted, this example is illustrative and that the sound processing unit 206L could include other types of input devices (e.g., telecoils, auxiliary input port, such as a Direct Audio Input (DAI), wireless transceivers, etc.) that receive input signals.

The input signals from any of these or other input devices could be used to generate input data for wireless streaming to the sound processing unit 206R.

Figure 5:
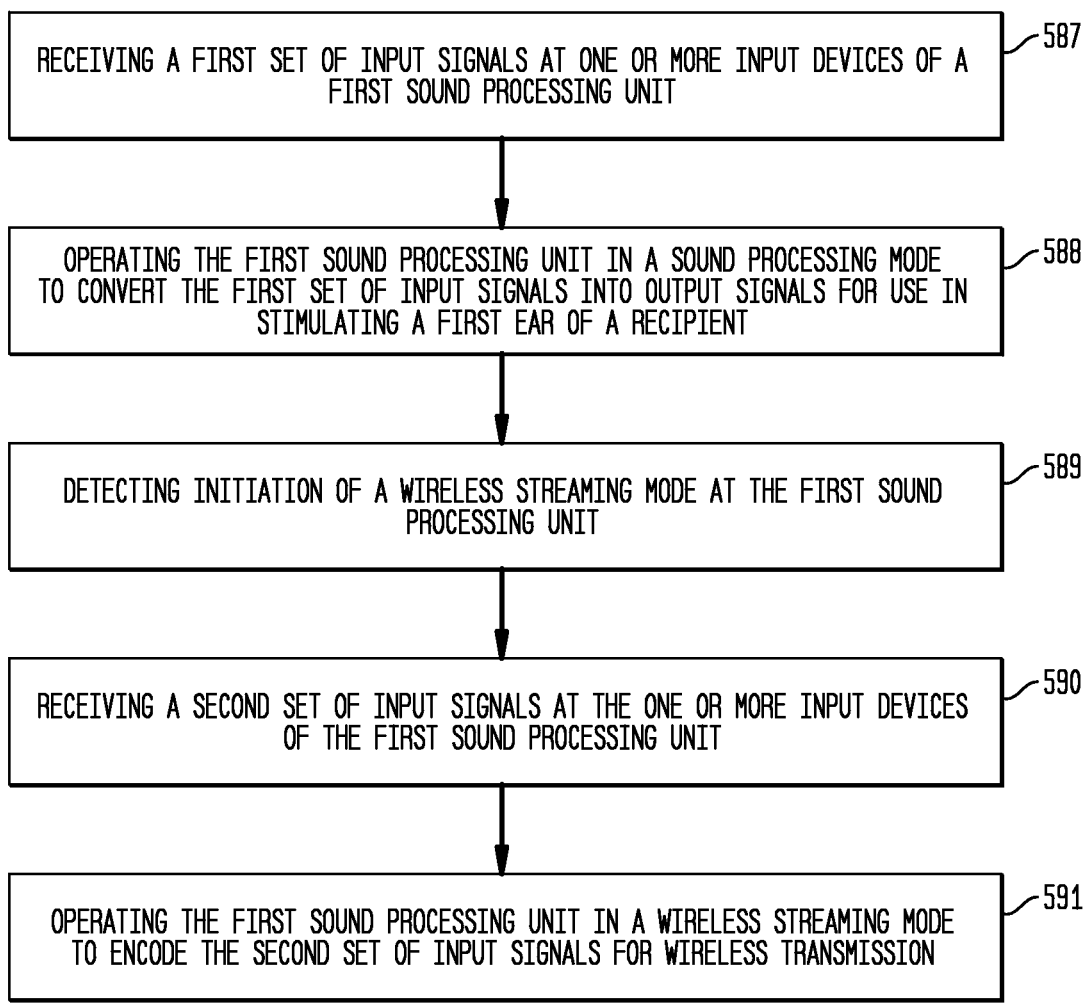
FIG. 5 is a flowchart of a method, according to certain embodiments.

FIG. 5 is a flowchart of a method 586 in accordance with embodiments presented herein. Method 586 begins at 587 where one or more input devices of a first sound processing unit receive a first set of input signals. At 588, while operating in a sound processing mode, the first sound processing unit converts the first set of sound signals into output signals for use in stimulating a first ear of a recipient. At 589, the first sound processing unit detects initiation of a wireless streaming mode. At 590, the first sound processing unit receives a second set of sound signals at the one or more input devices of the first sound processing unit. At 591, while operating in a wireless streaming mode, the first sound processing unit converts the second set of input signals into wireless packets. The first sound processing unit may then wireless transmit the wireless packets to a second sound processing unit.

Embodiments of the present invention have been primarily described above with reference to the use of two sound processing units each worn by the recipient. It is to be appreciated that embodiments of the present invention may also be implemented in embodiments that include two or three sound processing units and in which one of the sound processing units is not worn by the recipient. For example, a recipient could carry a supplemental sound processor for various reasons and this supplemental processor could be configured to perform the wireless streaming operations described herein (i.e., to function as a wireless accessory to wireless stream input data to one or two sound processing units worn by the recipient).

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A sound processing unit of a hearing prosthesis system, comprising:
   one or more input devices;
   a wireless transceiver; and
   one or more processors configured to:
      operate in a sound processing mode to convert input signals received at the one or more input devices into output signals for use in stimulating a first ear of a recipient, and
      selectively operate in a wireless streaming mode to encode input signals received at the one or more input devices and wirelessly transmit the encoded input signals by the wireless transceiver, wherein the wirelessly transmitted encoded input signals are at least partially used in stimulating a second ear of the recipient.

2. The sound processing unit of claim 1, wherein the one or more processors are configured to automatically initiate the wireless streaming mode in response to detection of one or more triggering conditions.

3. The sound processing unit of claim 2, wherein the sound processing unit comprises an accelerometer, and wherein the one or more triggering conditions include detection of at least one of a predetermined orientation or predetermined motion by the accelerometer.

4. The sound processing unit of claim 2, wherein the sound processing unit comprises:
   a coil configured to be inductively coupled to an implantable component;
   wherein the one or more triggering conditions include detection of loss of coupling between the coil and the implantable component and receipt of predetermined data from a second sound processing unit.

5. The sound processing unit of claim 4, wherein the predetermined data from the second sound processing unit is data indicating that the second sound processing unit is worn by the recipient.

6. The sound processing unit of claim 1, further comprising a user interface and wherein the one or more processors are configured to automatically initiate the wireless streaming mode in response to a user input at the user interface.

7. The sound processing unit of claim 1, wherein in the wireless streaming mode, the one or more processors are configured to:
   compress input signals received at the one or more input devices; and
   encode the compressed input signals into wireless packets for wireless transmission by the wireless transceiver.

8. The sound processing unit of claim 1, wherein the sound processing unit comprises a user interface, and wherein the one or more processors are configured to adjust operation of the user interface when in the wireless streaming mode.

9. The sound processing unit of claim 1, wherein the one or more input devices include a plurality of microphones forming a microphone array, and wherein in the wireless streaming mode, the one or more processors are configured to:
   adjust a directionality of the microphone array.

10. A method, comprising:
    receiving a first set of input signals at one or more input devices of a first sound processing unit;
    operating the first sound processing unit in a sound processing mode to convert the first set of input signals into output signals for use in stimulating a first ear of a recipient;
    detecting initiation of a wireless streaming mode at the first sound processing unit;
    receiving a second set of input signals at the one or more input devices of the first sound processing unit; and
    operating the first sound processing unit in a wireless streaming mode to encode and wirelessly transmit the second set of input signals, wherein the wirelessly transmitted encoded second set of input signals are at least partially used in stimulating a second ear of the recipient.

11. The method of claim 10, further comprising:
    wirelessly transmitting the second set of input signals directly to a second sound processing unit.

12. The method of claim 10, further comprising:
    wirelessly transmitting the second set of input signals from the first sound processing unit to an external device via a first wireless link; and
    wirelessly transmitting the second set of input signals from the external device to a second sound processing unit via a second wireless link.

13. The method of claim 12, wherein the first and second wireless links utilize a same communication protocol.

14. The method of claim 13, wherein the second wireless link is a closely-coupled wireless link.

15. The method of claim 10, further comprising:
receiving the second set of input signals at a second sound processing unit; and
generating output signals for use in stimulating the second ear of the recipient at least partially based on the second set of input signals.

16. The method of claim 15, further comprising:
receiving input signals at one or more input devices of the second processing unit; and
generating output signals for use in stimulating the second ear of the recipient at least partially based on both the second set of input signals and the input signals received at the or more input devices of the second processing unit.

17. The method of claim 10, wherein detecting initiation of a wireless streaming mode at the first sound processing unit comprises:
receiving a predetermined user input at a user interface of the first sound processing unit.

18. The method of claim 10, wherein detecting initiation of a wireless streaming mode at the first sound processing unit comprises:
detecting one or more triggering conditions at the first sound processing unit.

19. The method of claim 18, wherein the first sound processing unit comprises an accelerometer, and wherein detecting one or more triggering conditions at the first sound processing unit comprises:
detecting at least one of a predetermined orientation or predetermined motion by the accelerometer.

20. The method of claim 18, wherein the first sound processing unit comprises a coil configured to be inductively coupled to an implantable component, and wherein detecting one or more triggering conditions at the first sound processing unit comprises:
detecting a loss of coupling between the coil and the implantable component; and
detecting receipt of predetermined data from a second sound processing unit indicating that the second sound processing unit is coupled to an implantable component.

21. The method of claim 10, wherein operating the first sound processing unit in a wireless streaming mode to encode the second set of input signals for wireless transmission comprises:
compressing the second set of input signals received at the one or more input devices; and
encoding the compressed second set of input signals into wireless packets for wireless transmission.

22. The method of claim 10, wherein the first sound processing unit comprises a user interface, and wherein the method further comprises:
when in the wireless streaming mode, adjusting operation of the user interface.

23. The method of claim 10, wherein the first sound processing unit comprises a microphone array, and wherein the method further comprises:
when in the wireless streaming mode, adjusting a directionality of the microphone array.

24. The method of claim 10, further comprising:
when in the wireless streaming mode, adjusting a physical arrangement of the first sound processing unit.

25. A hearing prosthesis system, comprising:
a first implantable component; and
a first external sound processing unit configured for communication with the first implantable component, wherein the first external sound processing unit comprises:
one or more input devices;
a wireless transceiver; and
a dual-mode sound processing module configured to selectively perform:
sound processing operations that convert input signals received at the one or more input devices into output signals for use in stimulating a first ear of a recipient, or
wireless streaming operations that encode input signals received at the one or more input devices and wirelessly transmit the encoded input signals by the wireless transceiver, wherein the wirelessly transmitted encoded input signals are at least partially used in stimulating a second ear of the recipient.

26. The hearing prosthesis system of claim 25, wherein the dual-mode sound processing module is configured to automatically initiate the wireless streaming operations in response to detection of one or more triggering conditions.

27. The hearing prosthesis system of claim 26, wherein the first external sound processing unit comprises an accelerometer, and wherein the one or more triggering conditions include detection of at least one of a predetermined orientation or predetermined motion by the accelerometer.

28. The hearing prosthesis system of claim 26, wherein the first external sound processing unit comprises:
an external coil configured to be inductively coupled to an implantable coil of the first implantable component;
wherein the one or more triggering conditions include detection of loss of coupling between the external and implantable coils and receipt of predetermined data from a second sound processing unit.

29. The hearing prosthesis system of claim 28, wherein the predetermined data from the second sound processing unit is data indicating that the second sound processing unit is worn by a recipient.

30. The hearing prosthesis system of claim 25, further comprising a user interface and wherein the dual-mode sound processing module is configured to automatically initiate the wireless streaming operations in response to a user input at the user interface.

31. The hearing prosthesis system of claim 25, wherein, when selectively performing the wireless streaming operations, the dual-mode sound processing module is further configured to:
compress input signals received at the one or more input devices; and
encode the compressed input signals into wireless packets for wireless transmission by the wireless transceiver.

* * * * *

UNITED STATES PATENT AND TRADEMARK OFFICE
CERTIFICATE OF CORRECTION

| | |
|---|---|
| PATENT NO. | : 11,357,982 B2 |
| APPLICATION NO. | : 16/758591 |
| DATED | : June 14, 2022 |
| INVENTOR(S) | : Jan Patrick Frieding |

It is certified that error appears in the above-identified patent and that said Letters Patent is hereby corrected as shown below:

On the Title Page

Item (12):
Please change "Friedling" to --Frieding--

Item (72) Inventor:
Please change "Jan Patrick Friedling, Grose Vale (AU)" to --Jan Patrick Frieding, Grose Vale (AU)--

Signed and Sealed this
Sixteenth Day of July, 2024

Katherine Kelly Vidal
*Director of the United States Patent and Trademark Office*